US006464707B1

(12) United States Patent
Bjerken

(10) Patent No.: US 6,464,707 B1
(45) Date of Patent: Oct. 15, 2002

(54) VACUUM-ASSISTED REMOTE SUTURE PLACEMENT SYSTEM

(76) Inventor: David B. Bjerken, 1543 Brentwood Dr., Marietta, GA (US) 30062

( * ) Notice: Subject to any disclaimer, the term of this patent is extended or adjusted under 35 U.S.C. 154(b) by 0 days.

(21) Appl. No.: 09/540,972

(22) Filed: Mar. 31, 2000

Related U.S. Application Data

(60) Provisional application No. 60/127,344, filed on Apr. 1, 1999.

(51) Int. Cl.⁷ .............................................. A61B 17/10
(52) U.S. Cl. ...................................................... 606/139
(58) Field of Search ................................. 606/139, 153, 606/148, 186

(56) References Cited

U.S. PATENT DOCUMENTS

| | | |
|---|---|---|
| 3,552,626 A | 1/1971 | Astafiev et al. |
| 3,561,448 A | 2/1971 | Peternel |
| 3,946,740 A | 3/1976 | Bassett |
| 4,027,608 A | 6/1977 | Arbuckle |
| 4,235,177 A | 11/1980 | Arbuckle |
| 4,294,255 A | 10/1981 | Geroc |
| 4,350,160 A | 9/1982 | Kolesov et al. |
| 4,406,237 A | 9/1983 | Eguchi et al. |
| 4,414,908 A | 11/1983 | Eguchi et al. |
| 4,417,532 A | 11/1983 | Yasukata |
| 4,437,465 A | 3/1984 | Nomoto et al. |
| 4,465,070 A | 8/1984 | Eguchi |
| 4,484,580 A | 11/1984 | Nomoto et al. |
| 4,552,148 A | 11/1985 | Hardy, Jr. et al. |
| 4,553,544 A | 11/1985 | Nomoto et al. |
| 4,557,265 A | 12/1985 | Andersson |
| 4,702,250 A | 10/1987 | Ovil et al. |
| 4,747,358 A | 5/1988 | Moll et al. |
| 4,766,898 A | 8/1988 | Hardy et al. |
| 4,841,888 A | 6/1989 | Mills et al. |
| 4,898,155 A | 2/1990 | Ovil et al. |
| 4,899,746 A | 2/1990 | Brunk |
| 4,927,428 A | 5/1990 | Richards |
| 4,990,153 A | 2/1991 | Richards |
| 5,037,021 A | 8/1991 | Mills et al. |
| 5,080,663 A | 1/1992 | Mills et al. |
| 5,084,058 A | 1/1992 | Li |
| 5,152,769 A | 10/1992 | Baber |
| 5,163,946 A | 11/1992 | Li |
| 5,180,392 A | 1/1993 | Skeie et al. |
| 5,196,023 A | 3/1993 | Martin |
| 5,290,298 A | 3/1994 | Rebuffat et al. |
| 5,304,220 A | 4/1994 | Maginot |
| 5,308,353 A | 5/1994 | Beurrier |

(List continued on next page.)

FOREIGN PATENT DOCUMENTS

| | | |
|---|---|---|
| WO | WO 96/09796 | 4/1996 |
| WO | WO 96/20647 | 7/1996 |

Primary Examiner—Rodney M. Lindsey
Assistant Examiner—James G Smith
(74) Attorney, Agent, or Firm—Merchant & Gould

(57) ABSTRACT

A method and device for suturing tissue, in which the device includes a tube of a size to be inserted into a surgical site, such as into an artery or heart valve annulus of a patient. The tube includes a suction opening laterally circumscribing at least a portion of the tube to allow fluid communication between the tissue of the patient at the surgical site and the bore of the tube. Also within the tube is a carriage for detachably holding at least one needle, in which the carriage is slidably movable within the bore near the suction opening of the tube. When the tube is properly positioned, a vacuum source is placed in fluid communication with the bore of the tube so that the tissue is drawn into the suction opening of the tube. The carriage is then slid within the bore so that the needles detachably held thereby traverse the tissue, thus quickly and efficiently placing sutures in the tissue at the surgical site.

21 Claims, 9 Drawing Sheets

U.S. PATENT DOCUMENTS

| | | |
|---|---|---|
| 5,332,402 A | 7/1994 | Teitelbaum |
| 5,336,233 A | 8/1994 | Chen |
| 5,374,275 A | 12/1994 | Bradley et al. |
| 5,387,221 A | 2/1995 | Bisgaard |
| 5,397,325 A | 3/1995 | Della Badia et al. |
| 5,403,328 A | 4/1995 | Shallman |
| 5,470,337 A | 11/1995 | Moss |
| 5,545,214 A | 8/1996 | Stevens |
| 5,549,122 A | 8/1996 | Detweilwer |
| 5,571,215 A | 11/1996 | Sterman et al. |
| 5,575,800 A | 11/1996 | Gordon |
| 5,591,180 A | 1/1997 | Hinchliffe |
| 5,630,825 A | 5/1997 | de la Torre et al. |
| 5,682,906 A | 11/1997 | Sterman et al. |
| 5,755,730 A | 5/1998 | Swain et al. |
| 5,792,153 A | 8/1998 | Swain et al. |
| 5,799,661 A | 9/1998 | Boyd et al. |
| 5,814,005 A | 9/1998 | Barra et al. |
| 5,860,990 A | 1/1999 | Nobles et al. |
| 5,860,992 A | 1/1999 | Daniel et al. |
| 6,030,370 A | 2/2000 | Kupka et al. |
| 6,030,392 A | 2/2000 | Dakov |

VACUUM-ASSISTED REMOTE SUTURE PLACEMENT SYSTEM

CROSS REFERENCE TO RELATED APPLICATIONS

This application claims priority to U.S. provisional application Ser. No. 60/127,344 filed Apr. 1, 1999, which is incorporated by reference.

BACKGROUND OF THE INVENTION

1. Field of the Invention

The present invention related generally to the field of surgical procedures and, in particular, to the placement of sutures in tissue. More specifically, the present invention relates to a device and method to suture tissue of a patient that is particularly advantageous for less invasive surgical procedures performed within the heart and great vessels.

2. Background Art

Various types of surgical procedures are currently performed to investigate, diagnose, and treat diseases of the heart and the great vessels of the thorax. Such procedures include replacement of mitral, aortic, and other heart valves, repair of atrial and ventricular septal defects, treatment of aneurysms, and other procedures which interventional devices are introduced into the interior of the heart of a great vessel.

Of particular interest to the present invention are intracardiac and intraluminal procedures for surgical treatment of heart valves and great vessels. According to recent estimates, more than 79,000 patients are diagnosed with aortic and mitral valve disease in U.S. hospitals each year. More than 65,000 mitral valve and aortic valve replacement procedures are performed annually in the United States.

A heart valve may be replaced using various techniques. The valve leaflets of the native valve are excised, and a replacement valve is secured in the valve position, usually by suturing the replacement valve to the natural valve annulus. Various types of replacement valves are in current use, including mechanical and biological prostheses, as well as homografts and autografts.

When investigating, diagnosis, or treating diseases of the heart and the great vessels of the thorax, many current techniques require a gross thoracotomy, usually in the form of a median sternotomy, to gain access into the patient's thoracic cavity. A saw or other cutting instrument is used to cut the sternum longitudinally, allowing two opposing halves of the anterior or ventral portion of the rib cage to be spread apart. A large opening into the thoracic cavity is thus created, through which the surgical team may directly visualize and operate upon the heart and other thoracic contents.

Cardiac surgery remained largely unchanged while other surgical specialties moved rapidly toward less invasive operations. In recent times, however, heart surgery has begun to turn in a minimally invasive direction. Less-invasive surgical procedures have recently been developed which avoid the need for gross thoracotomy, such as a median sternotomy. Patients can be placed on cardiopulmonary bypass machines using minimally invasive techniques, and instruments have been developed to access and operate on the contents of the thorax without having to open vastly the chest.

The minimally invasive techniques subject the patient to less trauma and less recovery time and development has been occurring at a feverish pace, fueled by the media and patient preference as well as commercial developments that have made minimally invasive heart surgery possible. These minimally invasive operations probably represent the infancy of a new era of cardiac surgery. In the future, many coronary bypass operations may be performed as ambulatory procedures with same day or next day discharge. Patients will return to full activity within a week. Cardiac valve procedures will remain inpatient procedures with hospital stays of approximately three days and return to normal activity will occur at two weeks.

At present, select coronary artery bypass procedures can be performed without the use of cardiopulmonary bypass or median sternotomy. Both mitral and aortic valve replacements can now be performed through limited incisions that avoid sternal splitting.

Regardless of the surgical technique employed, common to many cardiac surgical procedures is the need to place sutures in the heart or other tissue within the thoracic cavity. For example, in the case of heart valve replacement, the valve prosthesis is usually sutured to tissue on or around the patient's native valve annulus.

A particular problem for minimally invasive techniques involves placing sutures in heart or other tissue that is accessed from outside of the patient's chest through small access ports presents a variety of difficulties. For instance, maneuverability is often difficult due to the limited space between the ribs. Further, when accessing the contents of the thoracic cavity through an intercostal space, visibility is limited, thereby making it difficult to properly place the suture. Further, such procedures can become time-consuming, particularly when placing a single suture at a time. Placing sutures in an annulus of a heart valve for attachment of a replacement valve is especially challenging. The suture needle must be inserted through the valve annulus in a direction toward or away from the surgeon, creating difficulty in seeing and manipulating the needle as it passes through the annulus.

Frequently, a curved needle is used in order to drive the needle deeper into the annulus tissue so that the suture will not tear out of the tissue. However, such a curved needle must be driven in an arc about an axis parallel to the plane of the annulus, whereas in less-invasive procedures, the surgical approaches used to access the heart valves dictate that the needle holding instrument be oriented at an angle perpendicular to the plane of the annulus. The needle must therefore be driven in a curved path about an axis roughly perpendicular to the shaft of the instrument. With the angular motion of the instrument highly limited when positioned through a small intercostal access port, the ability to drive a curved needle in an accurate path through the valve annulus is greatly compromised.

What is needed, therefore, are devices and methods for improved suture placement when access to the tissue is limited, such as in less-invasive surgical procedures. In particular, the devices and methods should reduce the size of the incision needed to access the internal anastomotic site. The device should place uniformly precise suture bites within the interrupted suture line. The device should simplify the placement of sutures by simultaneously placing all sutures, necessary to affix a prosthesis, at once. The devices and methods should reduce the time required to place the suture.

SUMMARY OF THE INVENTION

The present invention addresses the needs in the art by providing a method and device for suturing tissue, in which the device includes a tube of a size to be inserted into a surgical site, such as into an artery of a patient. The tube includes a suction opening laterally circumscribing at least a portion of the tube to allow fluid communication between the tissue of the patient at the surgical site and the bore of the tube. Also within the tube is a carriage for detachably holding at least one needle, in which the carriage is slidably movable within the bore near the suction opening of the tube. When the tube is properly positioned, a vacuum source is placed in fluid communication with the bore of the tube so that the tissue is drawn into the suction opening of the tube. The carriage is then slid within the bore so that the needles detachably held thereby traverse the tissue, thus quickly and efficiently placing sutures in the tissue at the surgical site.

In an exemplary embodiment, the invention provides for the placement of sutures within the heart or great vessel that is accessed from outside the closed thoracic region. According to one exemplary method, the patient's heart valve is accessed through a small port in the patient's chest. The patient's diseased or damaged heart valve is excised using endoscopic intrumentation. The heart valve annulus is then ready to accept interrupted sutures used to affix a heart valve prosthesis.

The present invention provides surgeons a means for quickly and precisely placing annular sutures through the smallest possible skin incision. Utilization of the present invention will minimize trauma to the patient, provide precise placement of sutures in the annular plane, and dramatically reduce cross clamp time. The present invention, accordingly, replaces the most time consuming and technically challenging portion of minimally invasive valve replacement surgery with a few simple motions or actions by the surgeon.

DETAILED DESCRIPTION OF THE INVENTION

Figure 1:
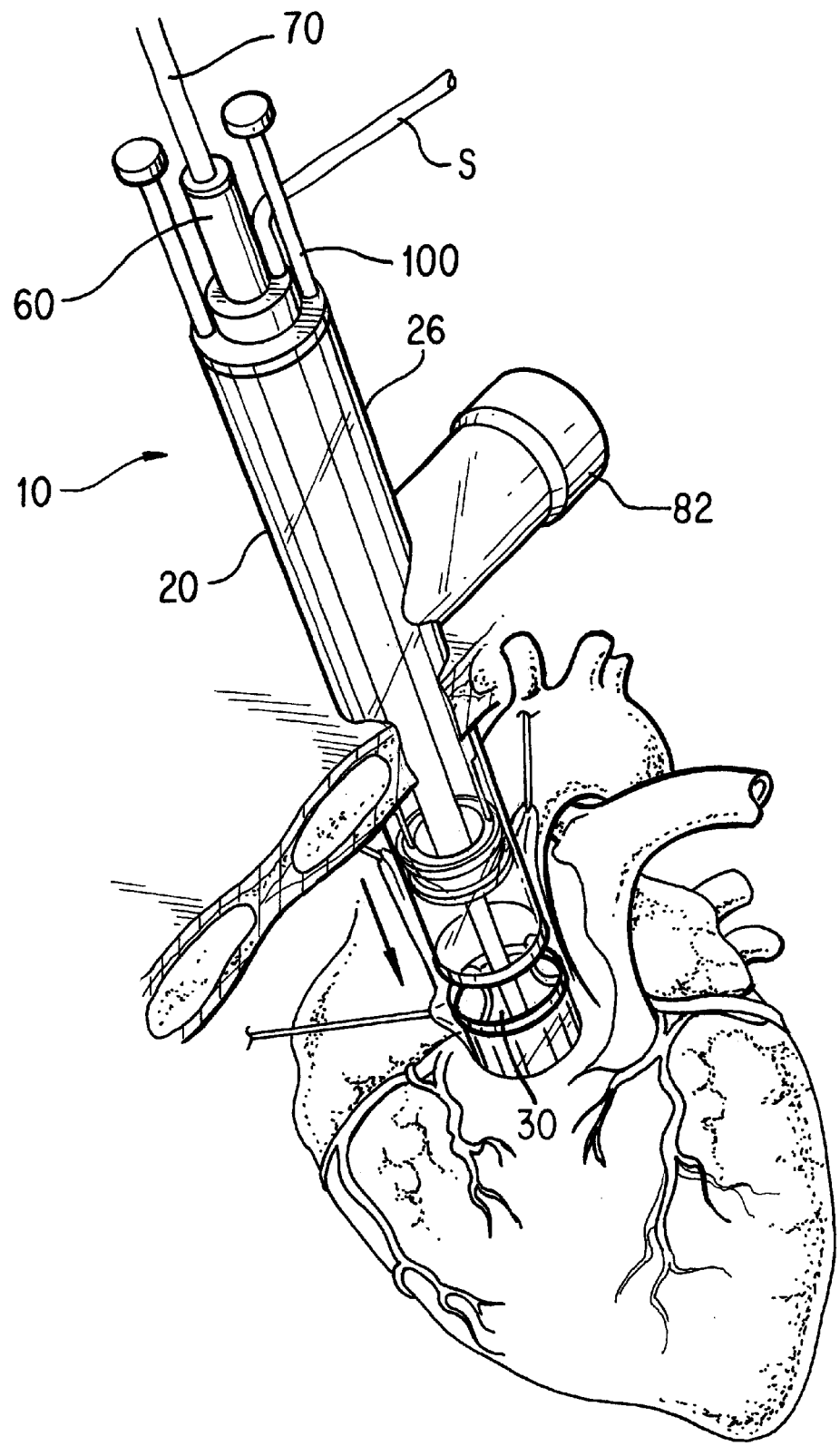
FIG. 1 is a perspective view of one embodiment of the device of the present invention being inserted into the aorta of a patient through a small access port in the patient's chest.

The present invention is more particularly described in the following examples that are intended as illustrative only since numerous modifications and variations therein will be apparent to those skilled in the art. As used in the specification and in the claims, "a," "an," and "the" can mean one or more, depending upon the context in which it is used. The preferred embodiment is now described with reference to the figures, in which like numbers indicate like parts throughout the figures.

The present invention provides for the placement of sutures in tissue structures (also interchangeably and broadly referred to as "tissue" herein), particularly in tissue that cannot be easily accessed using conventional instruments. As an overview, referring generally to FIGS. 1–4, the present invention comprises a suture device 10 having an elongated tube 20, a carriage 40 that detachably holds at least one needle 50, and a lifter 70 for moving the carriage 40 and associated needles 50 within the tube 20. The tube 20 defines an opening, specifically a suction opening 30, that is placed adjacent to the tissue to be sutured. A vacuum source 80, connected to the tube 20, is in fluid communication with the suction opening 30. When the vacuum source 80 is activated or energized, the tissue is drawn into the suction opening 30 of the tube 20. The surgeon, using the lifter 70, then moves the carriage 40 proximally within the stationary tube 20 so that the needles 50 detachably held by carriage 40 penetrate and traverse the tissue drawn into the suction opening 30. The needles 50 are then pulled entirely through the tissue. After the process is completed and the vacuum source 80 is de-energized, the tube 20 is removed from the surgical site and the sutures 56 manipulated in a manner known in the art to complete the surgical procedure.

The preferred embodiment of the present invention is ideal to deploy a substantially circular, uninterrupted suture line 56 in a vessel or hollow organ. Accordingly, the present invention is especially useful for placement of sutures in annular structures, such as a heart annulus. Examples of particular medical procedures requiring suturing that can be performed with the present invention include the replacement of heart valves (not shown), repair of aneurysms in the aorta and other locations, vascular grafting, and endolumninal repair of arteries. More specifically, the present invention may be used to attach mechanical valve prostheses, bioprostheses, homografts, allografts, and the like to a native annulus of the heart. The device 10 also can be used to repair sepal defects.

As one skilled in the art will appreciate, the present invention is especially useful in less invasive or endoscopic surgical procedures within an organ or vessel, particularly within the heart and great vessels of the thoracic cavity. As such, the present invention is especially advantageous for situations in which access to the thoracic cavity is obtained through percutaneous penetrations within intercostal spaces of the patient's rib cage, which is accomplished by surgical procedures that do not involve cutting, removing, or significantly displacing any of the patient's ribs or sternum.

Figure 2:
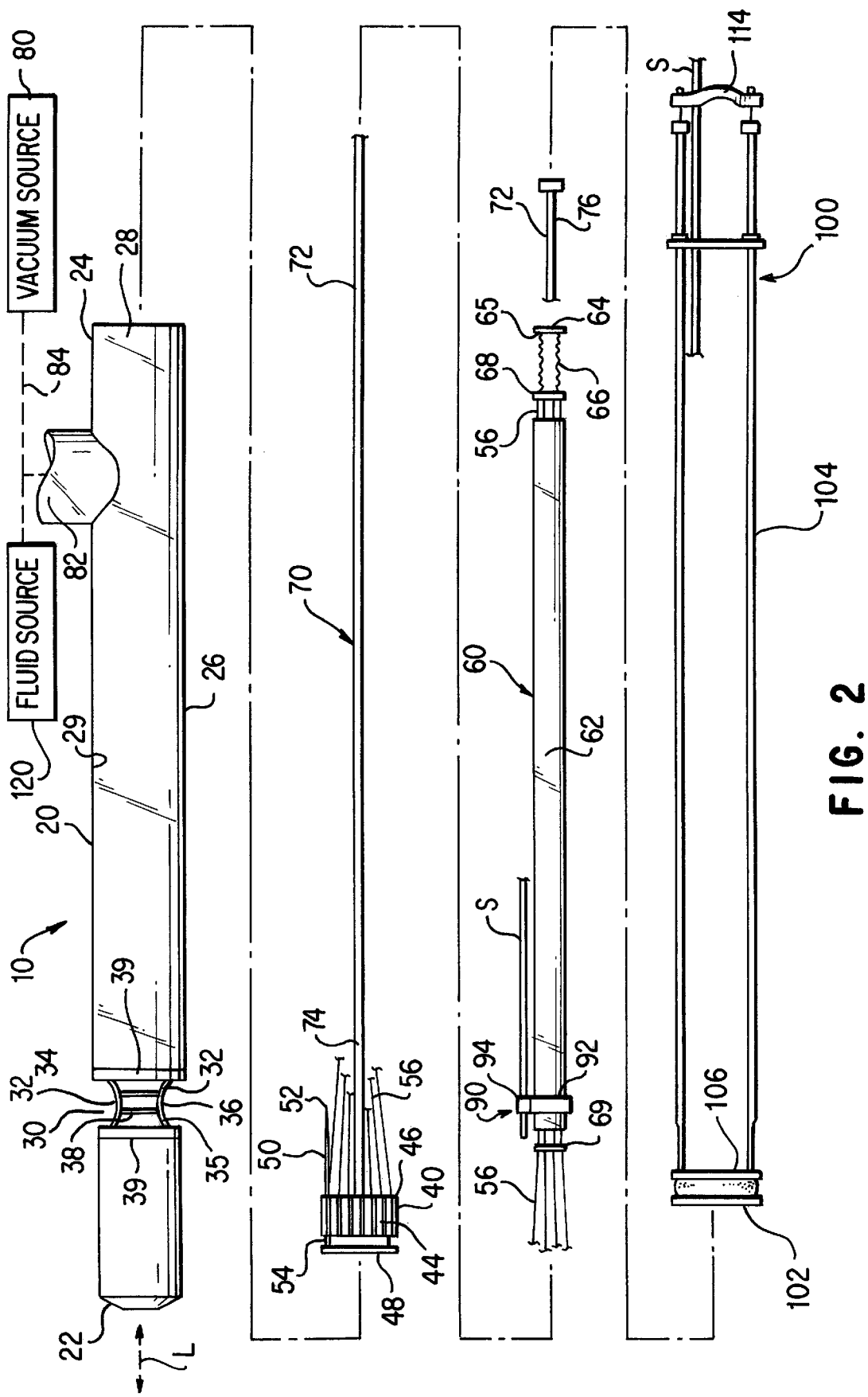
FIG. 2 is an exploded perspective view of the device of the present invention, showing schematically a vacuum source and a fluid source.

Returning to discussion of the device 10 of the present invention, in the presently preferred embodiment shown in FIGS. 1 and 2, the tube 20 has a distal end 22, a proximal end 24, a longitudinal axis L, and an exterior surface 26. The tube 20 also defines a bore 28 longitudinally extending intermediate the distal and proximal ends 23, 24, in which the bore 28 forms the interior surface 29 of the tube 20. In the preferred embodiment, the bore 28 extends the length of the tube 20. As shown, the bore 28 of the tube 20 is closed at the distal end 22 and opened at the proximal end 24. Preferably, the tube 20 is formed of a surgical-grade, clear plastic or polymer, such as a polycarbon material or the like, which allows visualization through the tube 20 via a scope S or other camera means, as discussed below.

The tube 20 also includes the suction opening 30 that circumscribes laterally (i.e., at a non-parallel angle to the longitudinal axis L) at least a portion of the tube 20 to allow fluid communication between the exterior surface 26 and the bore 28. As shown in FIGS. 1 and 2, the suction opening 30 is preferably located closer to the distal end 22 of the tube 20 than to its proximal end 24. Also, the suction opening 30 in the embodiment shown circumscribes the entire perimeter or circumference of the tube 20. It is also contemplated, as discussed below, that the suction opening 30 extends around only a portion of the perimeter or circumference of the tube 20. That is, for a tube 20 having a circular cross-section, the suction opening 30 of the illustrated embodiment laterally extends entirely around (i.e., 360 degrees) the tube 20, but contemplated embodiments use a suction opening 30 that extends only partially around the tube 20, such as half way (i.e., 180 degrees) or some smaller fraction around the circumference of the tube 20.

Although the tube 20 can take any desired shape, it preferably has a circular cross-section as shown in FIG. 1. The presently preferred tube 20 is also linear along is longitudinal axis L, but other curved shapes are also contemplated, such as a "banana" shape. As one skilled in the art will appreciate, the tube 20 can be shaped as desired to be complementarily received into the surgical site at which the device 10 will be used, e.g., into the aorta. Thus, the outer diameter and length of the tube 20 are sized accordingly based on the surgical site and can be altered accordingly for different surgical sites of a patient and to accommodate different patients. The dimensions of one contemplated tube 20 is approximately thirty (30) centimeters in length, approximately ten to thirty-three (10–33) millimeters in diameter, and approximately one to two (1–2) millimeters in thickness between the exterior surface 26 and the interior surface 29.

Figure 4A:
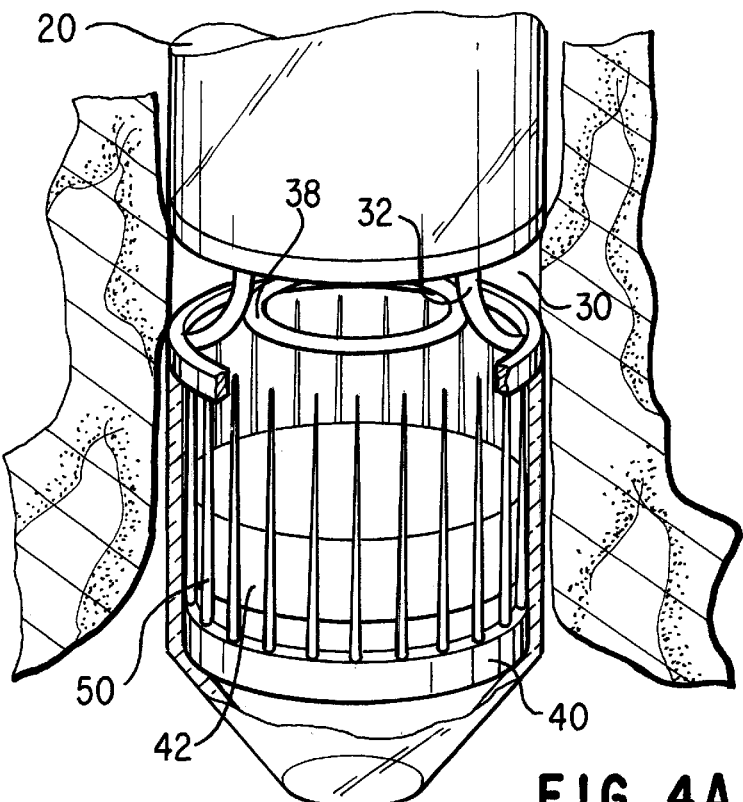
FIG. 4A is a side elevational view of the distal end of the device shown in FIG. 1 having been inserted into a surgical site, in which the tissue is shown partially cut away for clarity.

Other design features of the tube 20 include possibly coating the exterior surface 26 with an anti-thrombus-forming chemical. A special heparin coating applied to the exterior surface 26 of the tube 20 will help maximize visualization by minimizing clot formation on the tube 20. It is also preferred that the distal end 22 is curved and blunt—as opposed to having edges or corners—so that the distal end 22 atraumatically contacts the patient as the tube 20 is inserted, distal end 22 first, into the surgical site, such as the artery or other portion of the patient's body, which is illustrated in FIGS. 1 and 4A.

Referring back to FIG. 2, to support the structural integrity of the tube 20 adjacent the suction opening 30, it is preferred that the tube 20 also include a plurality of longitudinally-extending arcuate struts 32. Each arcuate strut 32 has an upper end 34 connected to a portion of the tube 20 adjacent to the suction opening 30 on the proximal side and an opposed lower end 35 connected to a portion of the tube 20 adjacent to the suction opening 30 on the distal side. Each arcuate strut 32 also has a body portion 36 intermediate the upper and lower ends 34, 35, which is disposed within the bore 28 of the tube 20. Thus, for the embodiment having a suction opening 30 that circumscribes the entire tube 20, the arcuate struts 32 hold together the portions of the tube 20 on each side of the suction opening 30 that would otherwise be freely separable from each other.

Although the arcuate struts 32 are shown as being substantially "C" shaped, other designs are contemplated. For example, the arcuate struts 32 can be substantially "V" shaped (oriented sideways when the tube 20 is upstanding), squared "U" shaped (oriented sideways when the tube 20 is upstanding), and the like. A desirable feature is that the body portion 36 of each strut 32 is disposed, at least partially, within the bore 28 of the tube 20. As will be discussed in more detail below, when the vacuum source 80 is activated, the tissue is pulled into the suction opening 30 so as to be located within the bore 28 of the tube 20, allowing the needles 50 to penetrate the tissue to place the suture 56 therethrough. As one skilled in the art will appreciate, the shape of the tissue drawn into the bore 28 of the tube 20 can be varied based on the shape of the arcuate struts 32 to obtain the proper suture "bite shape" and "bite size."

To support structurally the arcuate struts 32 and to help further shape the tissue drawn into the bore 28 of the tube 20 via the suction opening 30, the tube 20 also preferably includes at least one laterally-oriented band 38. Each band 38 is disposed within the bore 28 of the tube 20 and fixedly attached to a section of the body portion 36 of each arcuate strut 32 to circumscribe the struts 32. The struts 32 and bands 38 must be spaced apart from the interior surface 29 of the tube 20 at a sufficient distance to allow the needles 50 to pass therebetween as they suture the tissue drawn into the bore 28 of the tube 20 by the vacuum source 80.

In the presently preferred embodiment, the suction opening 30 includes four arcuate struts 32—ach spaced ninety degrees apart—and two bands 38. Other contemplated embodiments include six to ten arcuate struts 32 that are evenly spaced apart. Of course, as one skilled in the art will appreciate, the arcuate struts 32 must be of a dimension and separated so that they do not interfere with the needles 50 on the carriage 40 as the needles suture the tissue during the surgical procedure. In addition, another consideration is the effect of the vacuum translated to the tissue adjacent the suction opening 30, in which the greater surface area or mass of arcuate struts 32 and bands 38 may reduce the vacuum applied to the tissue through the suction opening 30.

Although the struts 32 can be fixedly attached or otherwise connected directly to the tube 20, in the presently preferred embodiment two rings 39 are used that have the same dimension as the exterior surface 26 of the tube 20 along its cross-section. As shown in FIG. 2, one ring 39 forms the proximal side of the suction opening 30 and the other ring 39 forms the distal side of the suction opening 30. Thus, the rings 39 attach to the tube 20 and the struts 32 connect to the rings 39, which improves the structural integrity of the device 10.

The struts 32, bands 38, and rings 39 can be made of metal (such as stainless steel, titanium and metal alloys), polymers, and the like. Preferably, the struts 32 and bands 38 are less than one (1) millimeter in caliber. The struts 32 can be formed as linear members and bent or arched into the desired shape. The struts 32, bands 38, and rings 39 can be connected to each other by welding, brazing, soldering, and the like. Alternatively, one or more of the components can be cast.

Also for the embodiment of the tube 20 in which the proximal portion of the tube 20 above the suction opening 30 is not directly connected to the distal portion of the tube 20 below the suction opening 30, it is contemplated that the distal portion have a smaller diameter than the proximal portion, although the components could have the same diameter. Additionally, it is desired that the bore 28 adjacent its distal end 22 decrease in its width or diameter to form a "shelf" on which the bottom portion 48 of the carriage 40 may rest and be positioned.

The device 10 of the present invention also preferably includes the carriage 40 for detachably holding at least one needle 50 and, more preferably a plurality of needles 50. As shown in FIGS. 2 and 4A, the preferred embodiment of the carriage 40 has an outer periphery 42 of a size to be complementarily and slidably received within the bore 28 near, or proximal to, the suction opening 30. In the preferred embodiment, the carriage 40 is circular in top plan view, just as the tube 20 is circular in cross-section so as to be complementarily received therein. Thus, the outer periphery 42 of the carriage 40 has a diameter slightly less than that of the interior surface 29 of the tube 20 to be slidably movable along at least a portion of the bore 28. The carriage 40 can be engineered and designed so that the needles 50 held thereby engage the annular tissue in one of several ways, such as parallel to the longitudinal axis L of the tube 20.

Addressing briefly the needles 50 used in conjunction with the preferred embodiment of the present invention, it is preferred that straight needles 50 are used, each needle 50 having a top end 52 and a bottom end 54. In one contemplated embodiment, the needles 50 are approximately thirty-five to forty (35–40) millimeters in length. Examples of straight needles 50 for surgical applications are Ethicon's needle product number V-47. Of course, as discussed for the dimensions of the tube 20, the size of the needles 50 used with the present invention may also be varied based on the surgical site at which the present invention is used, as well as the shape and dimension of the suction opening 30.

To position and detachably hold each needle 50, the periphery 42 of the carriage 40 defines at least one slit 44 therein along a portion of the carriage 40. Each slit 44 is of a size to complementarily receive the bottom end 54 of one respective needle 50 therein. Still referring to FIGS. xxx, when received into the slit 44, the needle 50 is positioned between the carriage 40 and the interior surface 29 of the tube 20 and detachably held thereby. As shown, the slit 44 only extends through a portion of the width of the carriage 40 so that the needle 50 is not able to slip completely through the carriage 40, particularly when the top end 52 of the needle 50 engages and penetrates the portion of the tissue that is drawn into the suction opening 30 of the tube 20.

The periphery 42 of the carriage 40 may have a constant dimension between its top 46 and bottom 48. Alternatively, the diameter of the periphery 42 may vary as shown in FIG. 2 along its height. That is, the portion of the periphery 42 of the carriage 40 adjacent its top 46 has a dimension substantially the same as that of the interior surface 29 of the tube 20 and has the slits 44 therein, the portion of the periphery 42 adjacent the bottom 48 of the carriage 40 also has a dimension substantially the same as that of the interior surface 29, but does not have any slits 44, and the portion of the periphery 42 between the top 46 and bottom 48 sections is of a narrower dimension. Accordingly, the bottom end 54 of the needle 50 is disposed on bottom section 48 of the carriage 40 and the middle portion of the needle 50 is disposed through and supported by the slits 44 in the top 46 section of the carriage 40 so that the straight needle 50 is vertically supported by the carriage 40. The illustrated embodiment shown in FIGS. 1, 2, and 4A–4F carries approximately twelve to thirty-three (12–33) straight needles 50 circumferentially around the periphery 42 of the carriage 40.

The carriage 40 can be formed of a polymer such as plastic, rubber, metal, ceramic, fabric, a combination thereof, and the like. The slits 44 can be milled or molded in the side of the carriage 40, depending on the material that is used to form it.

It is also contemplated to use separate clips (not shown) held together, each clip holding a section of needles 50. That is, in this contemplated design, the carriage 40 is formed a plurality of clips, such as three, instead of using an integrally formed carriage 40. Additionally, the present invention contemplates using other means for detachably holding the needles 50 in addition to the carriage 40 embodiments. An example of such additional detachably holding means includes a carriage that uses a plurality of individual sleeves (not shown)–one for each needle–that are of a size to receive and detachably hold that needle.

In the preferred embodiment, each of the needles 50 is connected to a respective double-armed monofilament or braided suture 56, which is partially pulled, via the respective needle, through the tissue that is drawn into the suction opening 30. The support that the straight needles 50 receive from the carriage 40 and the interior surface 29 of the tube 20 maintains their substantially perpendicular relationship to the annular tissue drawn into the suction opening 30 as the needles 50 traverse the tissue. As will be discussed in more detail below, the carriage 40 can contain all the sutures 56 needed to attach a heart valve prosthesis to a patient's annulus.

Regardless of the means used to detachably hold the needles 50, it is advantageous to include a suture column 60 when a plurality of needles 50 is used during the surgical procedure. The respective sutures 56 connected to the needles 50 positioned on the carriage 40 or other detachably holding means are preferably organized before the suture placing process by segregating each strand in a suture column 60 and remain organized during the procedure. As shown best in FIG. 2, the suture column 60 includes a clear plastic cylinder 62 that is approximately thirty to seventy-five (30–75) centimeters in length, about ten to twenty-two (10–22) millimeters in diameter, and approximately one (1) millimeter in thickness. The clear, straight, plastic cylinder 62 allows visualization of the sutures 56, which helps reduce the possibility of entanglement. Alternatively, the cylinder 62 can be formed of metal or other opaque material. At the proximal end 24 of the cylinder 62, a suture column top cap 64 is used that is made of any suitable plastic having a dimension to cover the top of the cylinder 62. There is a central hole in the suture column top cap 64 to accommodate the shaft 72 (which is discussed below) used to move the carriage 40 within the bore 28 of the tube 20. The suture column top cap 64 includes at least one attachment point 65 for a suture tension band 66 or spring, which is also attached to a suture end holder 68. At the bottom of the cylinder 62 is included a suture column bottom cap 69, which is similar in design to the top cap 64. However, unlike the top cap 64, the bottom cap 69 does not include the attachment points, but does include a plurality of holes, one for each needle 50 on the carriage 40. The bottom cap 69 and the suture end holder 68 also both include a central hole and are similarly formed of suitable plastic. Alternatively, the suture column 60 can be formed without a bottom cap 69.

Each individual suture 56 enters the suture column cylinder 62 through its own designated hole in the bottom cap 69 and extends and remains taut by the suture end holder 68. Each individual suture 56 can included a second needle (not shown), different from the needle 50 detachably held by the carriage at the other end of the suture 56. This second needle, for example, can be a half circle needle or other design known in the art that is adapted to suture the circumference of a heart valve prosthesis (not shown) or other device. After the tube 20 is removed from the surgical site and taken apart, this design facilities suturing the prosthesis using the second needles and sliding the prosthesis into the surgical site, specifically to engage and contact the tissue sutured by the needles 50 on the carriage 40, to complete the surgical procedure. As one skilled in the art will appreciate, attachment of the prosthesis to the tissue is best accomplished using a non-everting mattress suture or a simple interrupted suture.

The suture end holder 68 is distally movable within the cylinder 62 against the proximally-directed pulling force of the suture tension band 66. Thus, the suture 56 is fully extended within the cylinder 62 and held at a slight tension by the suture tension band 66. The suture end holder 68, nonetheless, is movable against the tension of the band 66, allowing the sutures 56 to be withdrawn from the suture cylinder 62 through the bottom cap 69 under control as needles 50 detachably held on the carriage 40 are passed into the annular tissue drawn into the suction opening 30 of the tube 20.

The device 10 also preferably includes a lifter 70 for moving the carriage 40, which detachably holds the needles 50, within the bore 28 of the tube 20 toward the suction opening 30. As best shown in FIG. 2, the preferred embodiment of the lifter 70 comprises a shaft 72 or engagement rod having a lower end 74 connected to a portion of the carriage 40, preferably in a central hole formed in the center of the top portion of the carriage 40, and an upper end 76 extending out of the proximal end 24 of the tube 20. A preferred embodiment of the shaft 72 is approximately fifty-five to eighty (55–80) centimeters in length and two to four (2–4) millimeters in diameter. Preferably, the shaft 72 is made of plastic, metal, fiberglass, carbon, or the like.

When a proximally-directed pulling force is applied to the shaft 72 adjacent its upper end 76, the carriage 40 moves proximally within the bore 28 of the tube 20, causing the needles 50 detachably held within the respective slits 44 correspondingly to slide along the interior surface 29 of the tube 20 toward the suction opening 30. Accordingly, for the embodiment shown in FIGS. 1, 2, and 4A–4E, when the surgeon pulls on the portion of the shaft 72 extending out of the proximal end 24 of the tube 20, the pulling force causes the needles 50 to move within the bore 28 so that the top ends of the needles 50 pass by the suction opening 30 to pierce the portion of the tissue that has been moved or drawn therein. As the needles 50 move proximally, the attached sutures 56 follow by exiting the bottom cap 69 of the suture column 60.

In addition to the lifter 70, the present invention also contemplates other means for moving the carriage 40 within the bore 28 of the tube 20 toward the suction opening 30. For example, one contemplated embodiment is a balloon (not shown) or other expandable member that is placed between the closed distal end 22 and the carriage 40 or other means for detachably holding the needles 50. A fluid, preferably a liquid, is used to expand the balloon by injection, for example, through a conduit (not shown) originating from outside the tube 20, through the proximal end 24 of the tube 20, and along the length of the bore 28 (traversing the center of the carriage 40). The fluid is injected into the balloon at a pressure above atmospheric and, since the balloon is a closed volume, the fluid, acting as a hydraulic pressure, causes the balloon to expand. Once the balloon expands to fill the volume between the closed distal end 22 of the tube 20 and the underside of the carriage 40, additional expansion forces the carriage 40 to move proximally along the bore 28 of the tube 20. Thus, the result of the balloon pushing on the underside of the carriage 40 is the same as the surgeon pulling proximally on the lifter 70, as described above, pushing the suture needles 50 through the annular tissue. Alternatively, the volume formed by the bottom of the carriage 40, the distal end 22 of the tube 20, and the bore 28 can be closed except for the fluid conduit so that injection of the fluid into the closed volume forces the carriage 40 to move proximally, similar to operation of a piston.

The preferred embodiment to draw or pull the tissue to be sutured through the suction opening 30 of the tube 20 is the vacuum source 80. Referring again to FIG. 2, the tube 20 preferably includes a vacuum port 82 disposed intermediate the suction opening 30 and its proximal end 24 to which the vacuum source 80 is operably connected. The vacuum port 82 can be constructed of plastic, metal, rubber, or a combination or materials that are glued, plastic welded, or molded to the exterior surface 26 of the tube 20. In one embodiment, the vacuum port 82 is itself a conduit that is five to sixteen (5–16) centimeters in length and approximately twenty (20) millimeters in diameter. A vacuum source hose 84 (shown schematically) can latch to or screw onto the conduit forming the vacuum port 82. Regardless of the vacuum port design, the vacuum source 80 is in fluid communication with the bore 28 of the tube 20 and, accordingly, the vacuum source 80 is also in fluid communication with the suction opening 30. As one skilled in the art will appreciate, it may be advantageous to cover the proximal end 24 of the tube 20 if it is open to atmosphere so that the suction generated by the vacuum source 80 is applied only or predominantly to the suction port.

Since vacuum sources are well know, the vacuum source 80 is illustrated schematically. As one skilled in the art will appreciate, the vacuum source 80 may include a source to generate the vacuum (such as a pump or the like), a means to power or drive the source (such as electricity or manual power), and the vacuum source hose 84 or other conduit to interconnect the vacuum source 80 to the suction opening 30 of the tube 20.

It may also be desired to have a vacuum source 80 that is controllable to generate varying sub-atmospheric pressures. Thus, the surgeon may start at one vacuum pressure and lower the pressure (i.e., increase the vacuum) as necessary based on the condition, flexibility, or malleability of the tissue that is to be drawn into the suction opening 30 of the tube 20.

It is also contemplated that either (1) a single vacuum source 80 can be placed in fluid communication with the bore 28 of the tube 20 at multiple locations or (2) a plurality of vacuum sources can be placed in fluid communication with the bore 28 at multiple locations. For example, addressing the latter embodiment, one vacuum source 80 can be connected to the tube 20 at the vacuum port 82 as shown schematically in FIG. 2. Another, second vacuum source (not shown) can be connected to the upper end 76 of the shaft 72, which is formed as a hollow member, so that the second vacuum source takes a suction below (i.e., distally of) the bottom 48 of the carriage 40. Accordingly, in this design, the two vacuum sources each take a suction on either side (i.e., on the proximal and distal sides) of the suction opening 30, causing the tissue to be drawn into the suction opening 30 more evenly, instead of being pulled toward the proximal end 24 of the tube 20 with a single vacuum source 80 having a single connection to the bore 28 of the tube 20. The second vacuum source may need to be capable of drawing a larger vacuum since there will be more head loss and a narrower conduit through which the second vacuum source is connected to the bore 28 of the tube 20.

One skilled in the art will also appreciate that although the device 10 of the present invention is preferably not to be reused after a surgery on another patient, the vacuum source 80 can be used repeatedly for numerous operative procedures, as long as it does not become contaminated.

One skilled in the art will appreciate that while the present invention is ideal for operating on a patient in an endoscopic procedure, it can be used in other contexts. As such, it may be possible to use the device 10 of the present invention without the vacuum source 80 being required. For example, if the surgeon has fairly unrestricted access to the exterior of the tissue structure to be sutured, the surgeon could apply an external compressive pressure to cause the internal surface of the tissue to be forced into the suction opening 30, at which time the needles 50, via the carriage 40, would be moved to suture the tissue. In another embodiment, the diameter of the tube 20 can be wider than that of the annular tissue, causing the tissue adjacent the suction opening 30 to be drawn therein. Accordingly, although the preferred embodiment uses the vacuum source, the surgical procedure using the device 10 of the present invention can be performed without using one.

The present invention can also include an endoscope S or camera means to view the surgical site and ensure that the suturing procedure occurs properly. To support the scope S, a rotatable scope guide 90 can be included within the bore 28 of the tube 20. In the embodiment illustrated in FIG. 2, the scope guide 90 has a center portion 92 that engages the suture column cylinder 62. The scope guide 90 also includes a sleeve 94 or channel, which is of a size to complementarily receive the scope S, and the sleeve 94 is rotatable completely around (i.e., 360 degrees) the center portion 92 to allow the scope S to be movably positioned at different locations throughout the surgical procedure. The scope guide 90 can be formed of plastic, metal, or ceramic material.

Now addressing using the device 10 of the present invention to perform a surgical procedure, it is ideally suited to place sutures 56 in the annulus of a heart valve, as noted above. Before using the device 10 in such a procedure, however, the surgical site is accessed through a port in the patient's chest using techniques well known in the art. The patient's diseased or damaged heart valve is removed using minimally invasive techniques. Using thoracoscopic instrumentation and a video scope S, the tissue can be visualized, manipulated and resected.

After the diseased valve has been excised and the annulus has been sized thoracoscopically, the properly sized tube 20 is introduced through the chest wall, through the aortotomy, and into the valve annulus, which is shown in FIGS. 1 and 4A.

With endoscopic visualization using the scope S, the distal end 22 of the tube 20 is inserted into the port in the patient's chest and guided into the heart valve annulus. The video scope S or camera, located inside the bore 28 of the transparent tube 20, allows for precise placement of the suction opening 30 within the heart valve annulus. The distal portion of the tube 20, which houses the carriage 40 detachably holding the needles 50, is located interior to the heart valve annulus and proposed suture line 56. For example, if sutures 56 are to be placed in the aortic valve annulus, the distal end 22 of the tube 20 will be located within the left ventricle.

Figure 4B:
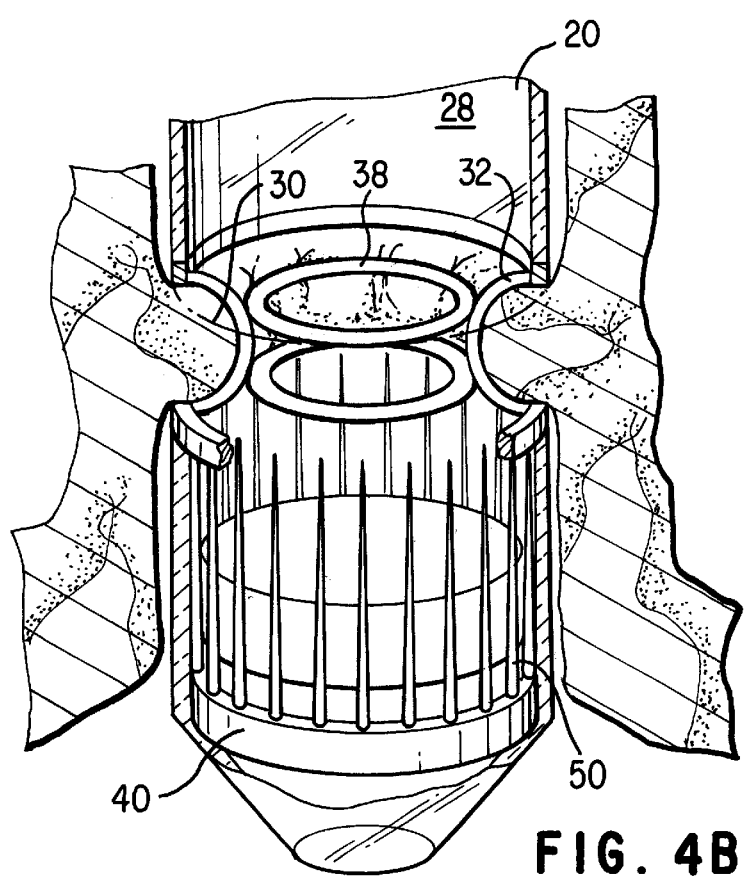
FIG. 4B is a view of FIG. 4A, in which a portion of the tissue has been drawn into the suction port.

When the suction opening 30 of the tube 20 is confirmed to be at the desired location as shown in FIG. 4A, the vacuum source 80 is activated. The suction created by the vacuum source 80 adjacent the suction opening 30 (i.e., the suture engagement zone of the annulus) draws the adjacent tissue into the shaped gap of the suction opening 30 of the tube 20, which is shown in FIG. 4B. The tissue that has been drawn into the suture bite zone is preferably cross-sectionally shaped in the form of a half circle. The endoscopic video scope or camera means within the tube 20 confirms whether the proper tissue has been drawn in through the suction opening 30 into the bore 28 of the tube 20.

Figure 4C:
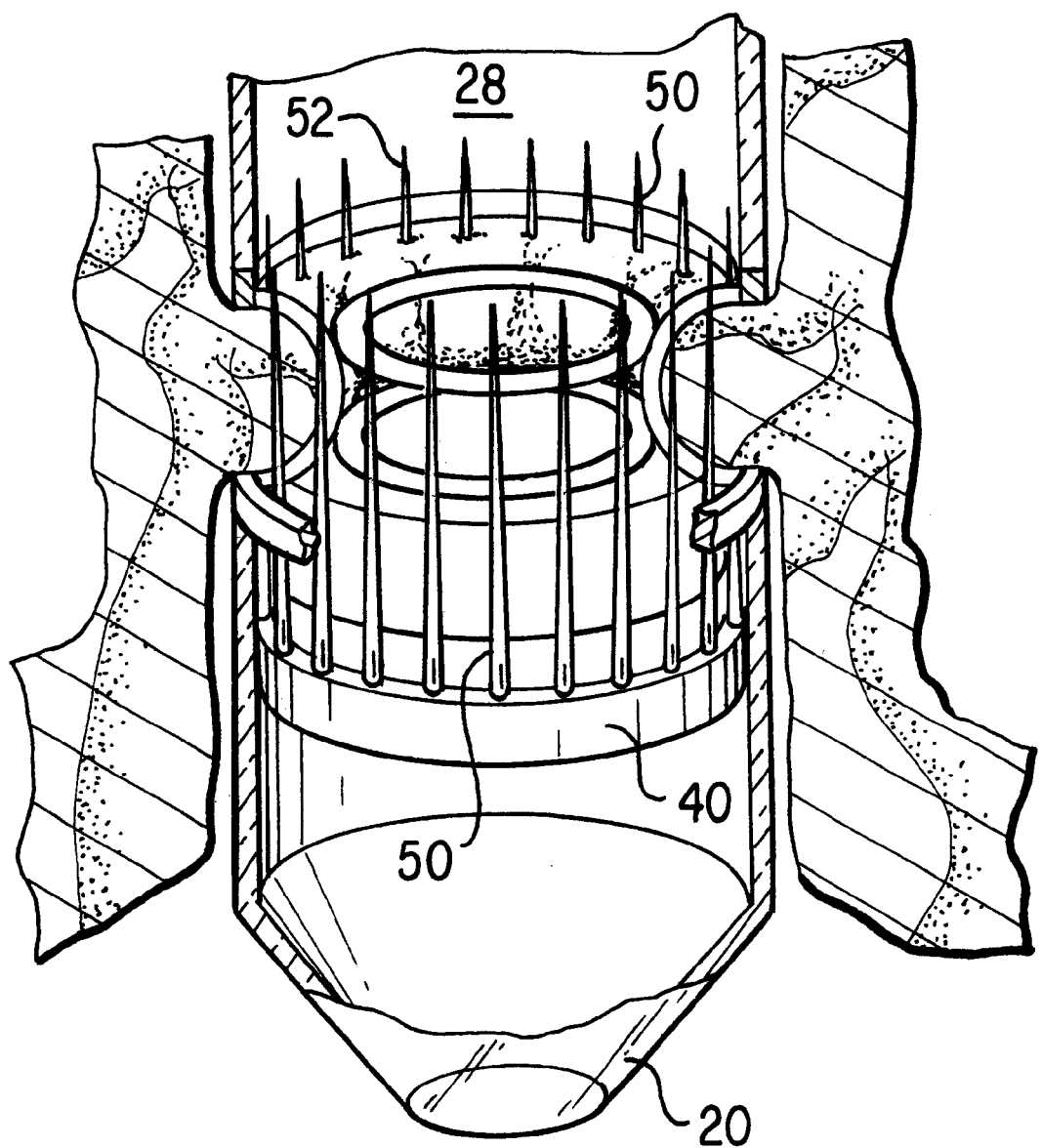
FIG. 4C is a view of FIG. 4B, in which the needles have been moved proximally so as to partially traverse the drawn-in tissue.

With the tissue drawn into the suction opening 30 as a result of the vacuum source or other means as shown in FIG. 4B, the carriage 40 is moved proximally using the shaft toward the drawn-in, annular tissue of the suture engagement zone, penetrating the tissue with the plurality of suture needles 50 detachably held by the carriage 40, as shown in FIG. 4C. The straight suture needles 50 transect the half circle-shaped tissue, "biting" sufficiently into the annular tissue. The video scope confirms proper needle 50 penetration through the tissue.

Still referring to FIG. 4C, each needle 50 that has penetrated the annular tissue has sufficient length to pass through the suture bite zone so that the top end 52 is re-exposed within the bore 28 proximal to the tissue. Tissue penetration by the suture needle 50 is confirmed with the video scope. The needles 50 are then simultaneously grasped and pulled up into the bore 28 proximally a centimeter or more using a suture engaging means.

Referring back to FIGS. 2 and 3, the suture engaging means 100 is another aspect of the present invention that assists the surgeon in effectively suturing the surgical site. The preferred embodiment is an engager 102 having an extender 104 connected to a grasping portion 106. The grasping portion 106 forms at least one slot 110 of a size to complementarily receive and detachably hold a portion of a needle 50 therein, specifically the portion of the needle 50 or needles that have proximally penetrated through the annular tissue drawn through the suction opening 30. The grasping portion 106 is movable within the bore 28 of the tube 20 between an engaging position and a removing position. In the engaging position (shown in FIG. 4D), the grasping portion 106 of the engager 102 is positioned near the suction opening 30 to be able to contact and detachably hold a portion of the needle 50 adjacent the top end 52. In the removing position, the grasping portion 106 is positioned closer to the proximal end 24 of the tube 20 (shown in FIG. 4E). Accordingly, during the surgical procedure when the surgeon moves the engager 102 from the engaging position to the removing position while the grasping portion 106 detachably holds a respective portion of a needle 50 therein, the needle 50 is pulled proximally, which causes the needle 50 to pass further through the annular tissue.

Figure 3:
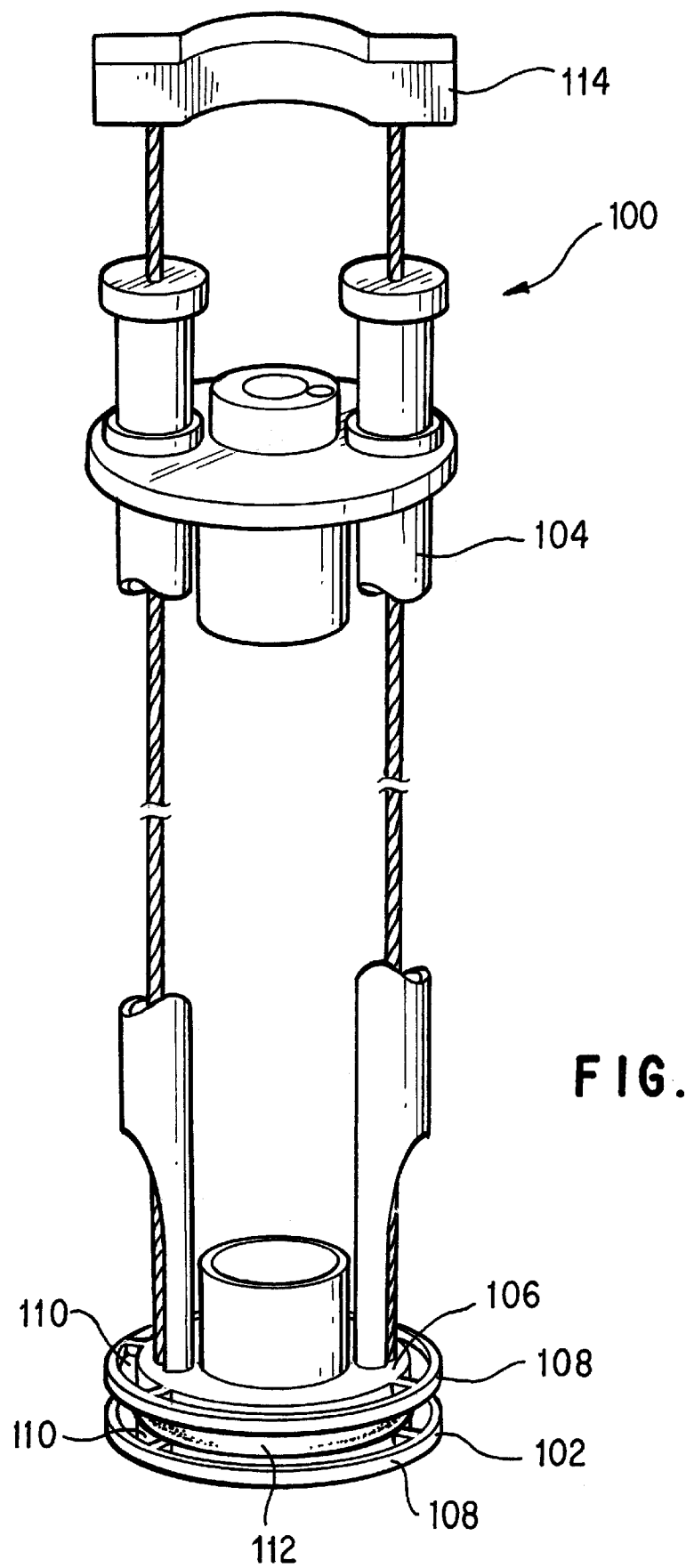
FIG. 3 is a side elevational view, partially cut away, showing a suture engager.

As best shown in FIG. 3, the preferred embodiment of the grasping portion 106 comprises at least two spaced apart rings 108 that hold a rubber 112, foam, or other malleable material therebetween. The rubber 112 also preferably is in the shape of a circle in plan view and has a smaller diameter than the two spaced apart rings 108. These rings 108, which are preferably formed of metal, ceramic, hard plastic, or the like, are movable relative to each other and have a slot 110 adjacent their outer edge of a size to receive a portion of each needle 50 therein. The rubber 112 is movable between an expanded and a compressed position by a puller 114. In operation, when the rubber 112 is in the expanded position and using the extender 104, a portion of each needle 50 is fed through the respective slots 110 of the two rings 108. The puller 114, which can be formed as a movable handle mounted to the extender 104, is then used to move the two rings 108 toward each other, causing the rubber 112 therebetween to move from the expanded position to the compressed position. The compressing rubber 112 expands outwardly toward the slots 110 and the portion of the needles 50 located within the slots 110 and between the two rings 108. When in the fully compressed position, the needles 50 are sandwiched and held by three points: the edges of the two slots 110 of the two rings 108 on one side and the rubber 112 on the other side. Thus, when the rubber 112 is in the compressed position, the needles 50 are detachably held by the grasping portion 106 of the engager 102. As such, the extender 104 attached to the grasping portion 106 can be pulled proximally so that the detachably held needles 50 that have passed partially through the annular tissue are correspondingly pulled proximally within the bore 28 of the tube 20. Also, if a suture column cylinder 62 is used in the device 10, the grasping portion 106 and extender 104 need to include a central opening of a size to slide over the suture column cylinder 62.

In another embodiment (which is not shown), the grasping portion comprises multiple rings with individual openings spaced apart and located to receive the suture needles. Thus, instead of having slots that can hold a plurality of needles therein, the individual openings each hold a single needle. Also, instead of including a center rubber, a middle ring is positioned between the two outer rings. Once the needles have passed through the openings in the three rings, the handle of the engager is twisted, turning the middle ring relative to the two outer rings. This twisting turns the middle ring so as to detachably hold the needles with a three point compression formed by the edge of the openings of the three rings. As one skilled in the art will appreciate, the embodiment shown in FIG. 3 is easier to use than the embodiment being described in this paragraph since there is more room and play to receive the portions of the needles therein.

Of course, one skilled in the art also appreciates that the needles 50 can be pulled or moved proximally using other techniques, such as individually and manually pulling each needle 50 proximally within the bore 28 of the tube 20.

Figure 4D:
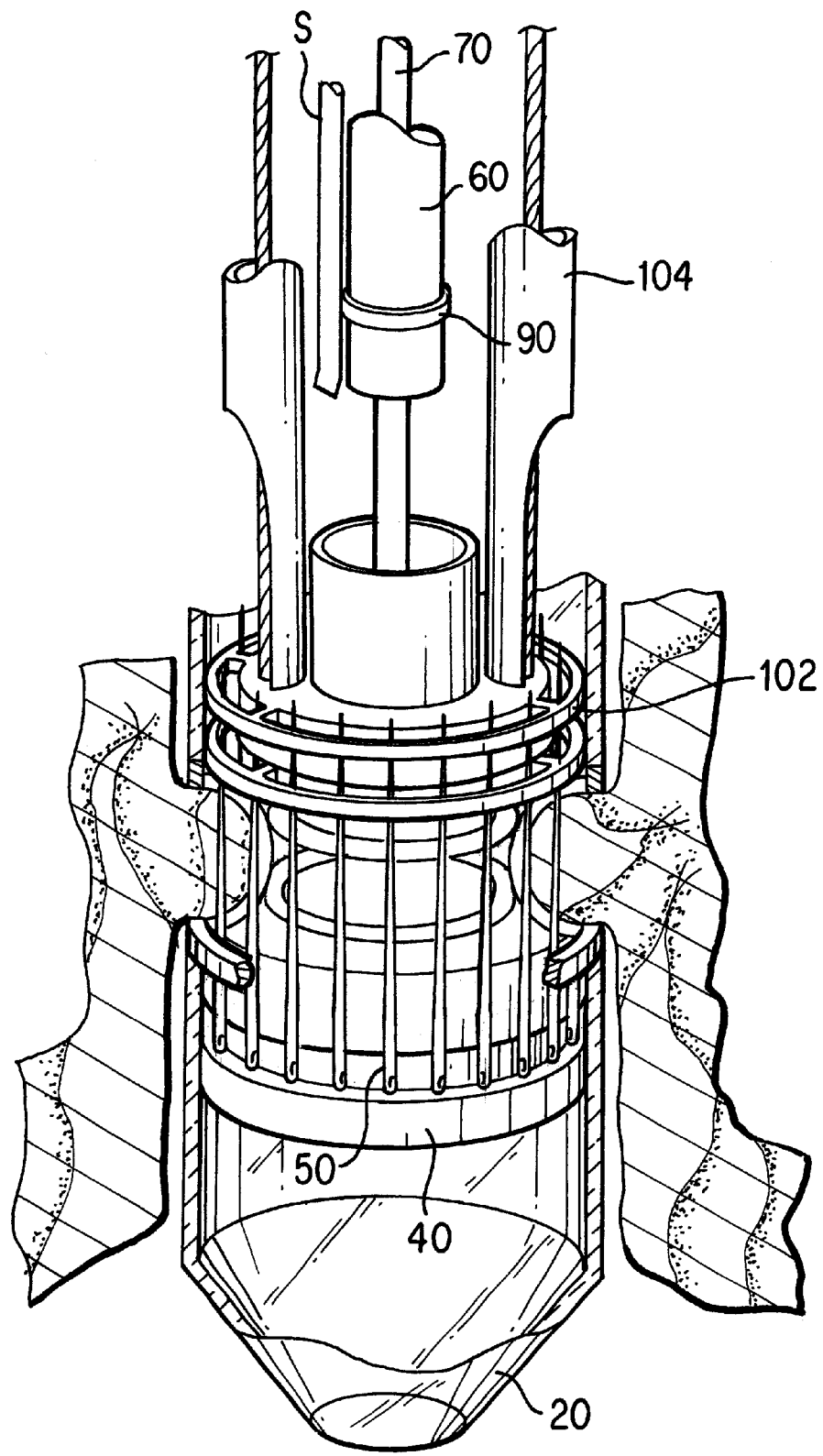
FIG. 4D is a view of FIG. 4C, in which the suture engager shown in FIG. 3 has engaged the top portion of the needles that have partially traversed the drawn-in tissue.
Figure 4E:
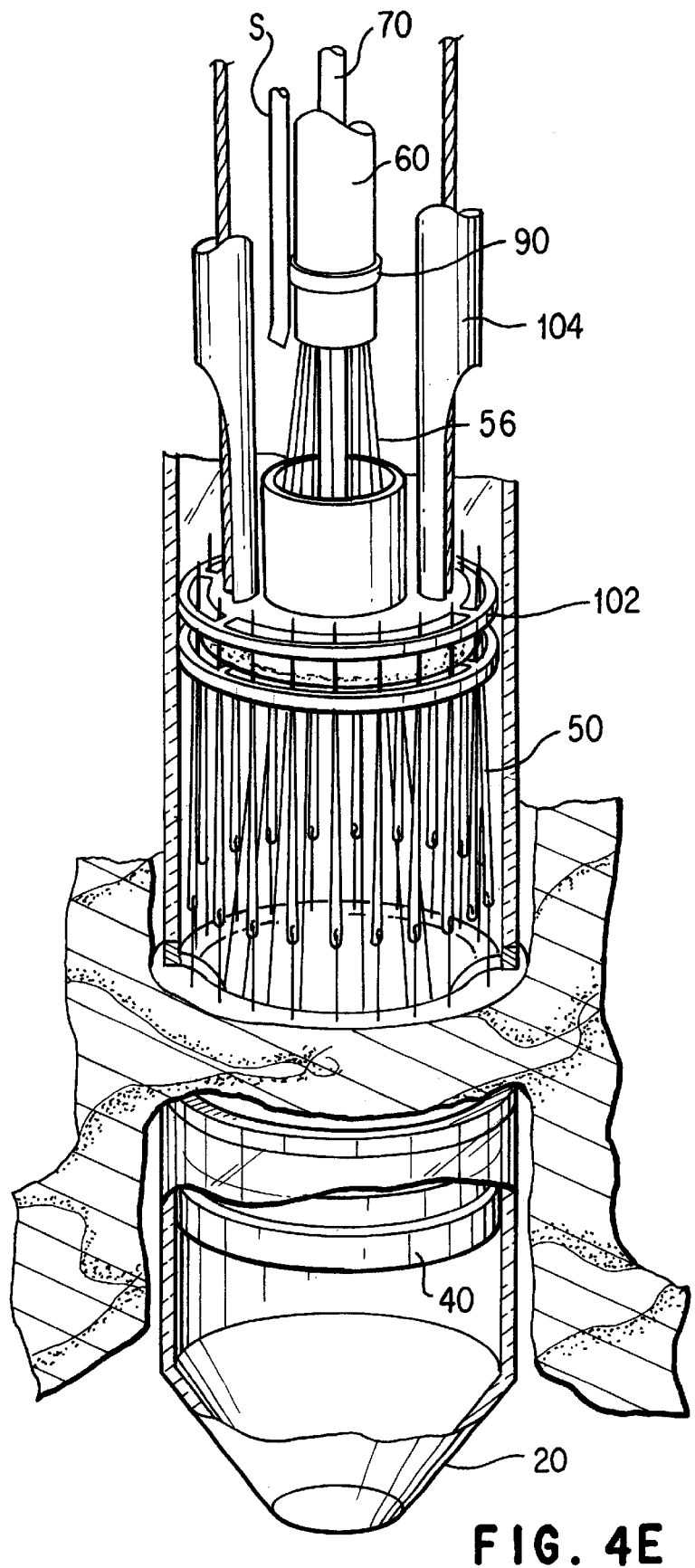
FIG. 4E is a view of FIG. 4D, in which the suture engager has pulled the needles through and out of the drawn-in tissue.

Returning to the method of the present invention shown in FIG. 4D, using the preferred embodiment of the engager 102, the video scope S confirms the capture of all the needles 50 with the grasping portion 106 when the rubber 112 is in the compressed position. After this verification, the surgeon pulls the extender 104 proximally within the bore 28 of the tube 20 so that the needles 50 are correspondingly pulled proximally at least an inch, causing the bottom ends 54 of the needles 50 to exit the tissue and leaving just the suture material 56 within the tissue, which is shown in FIG. 4E.

Figure 4F:
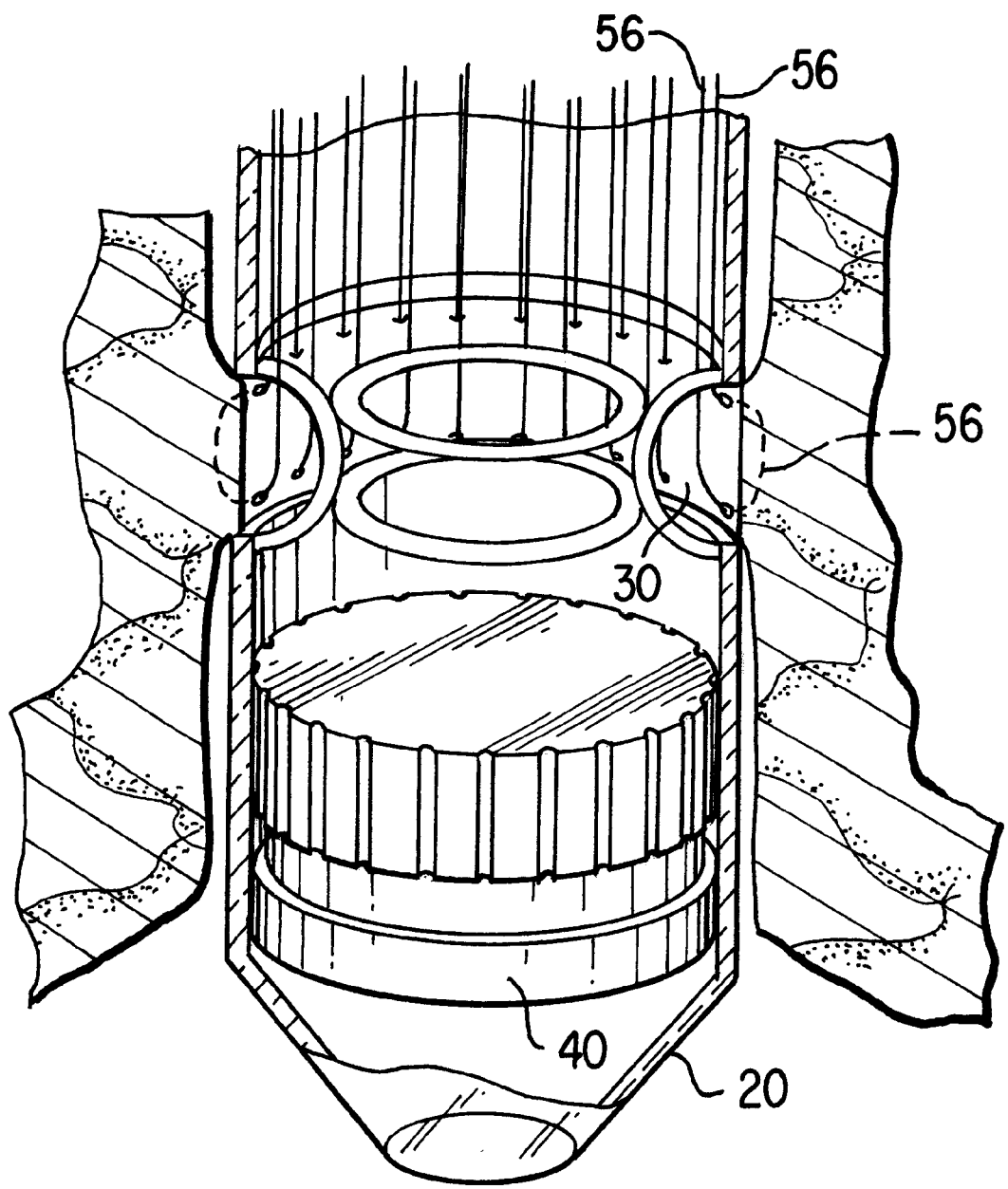
FIG. 4F is a view of FIG. 4E, in which the sutured tissue has returned to its position outside the suction opening of the tube.

The vacuum source 80 is then deactivated and the drawn-in tissue, now containing sutures 56, retracts from the suction opening 30, as shown in FIG. 4F. To ensure that the tissue fully exits from the suction opening 30, the present invention optionally includes a means to inject a fluid into the bore 28 of the tube 20 so that the fluid is in communication with the suction opening 30. Accordingly, the bore 28 of the tube 20 is preferably connected to a liquid source 120 (shown in FIG. 2) so that saline or other similar solutions can fill a portion of the bore 28, exiting through the suction opening 30. The pressure from the saline within the tube 20 pushes the sutured tissue at the suction opening 30 clear of the bore 28 of the tube 20, allowing easy withdrawal of the tube 20, which is shown in FIG. 4G.

Figure 4G:
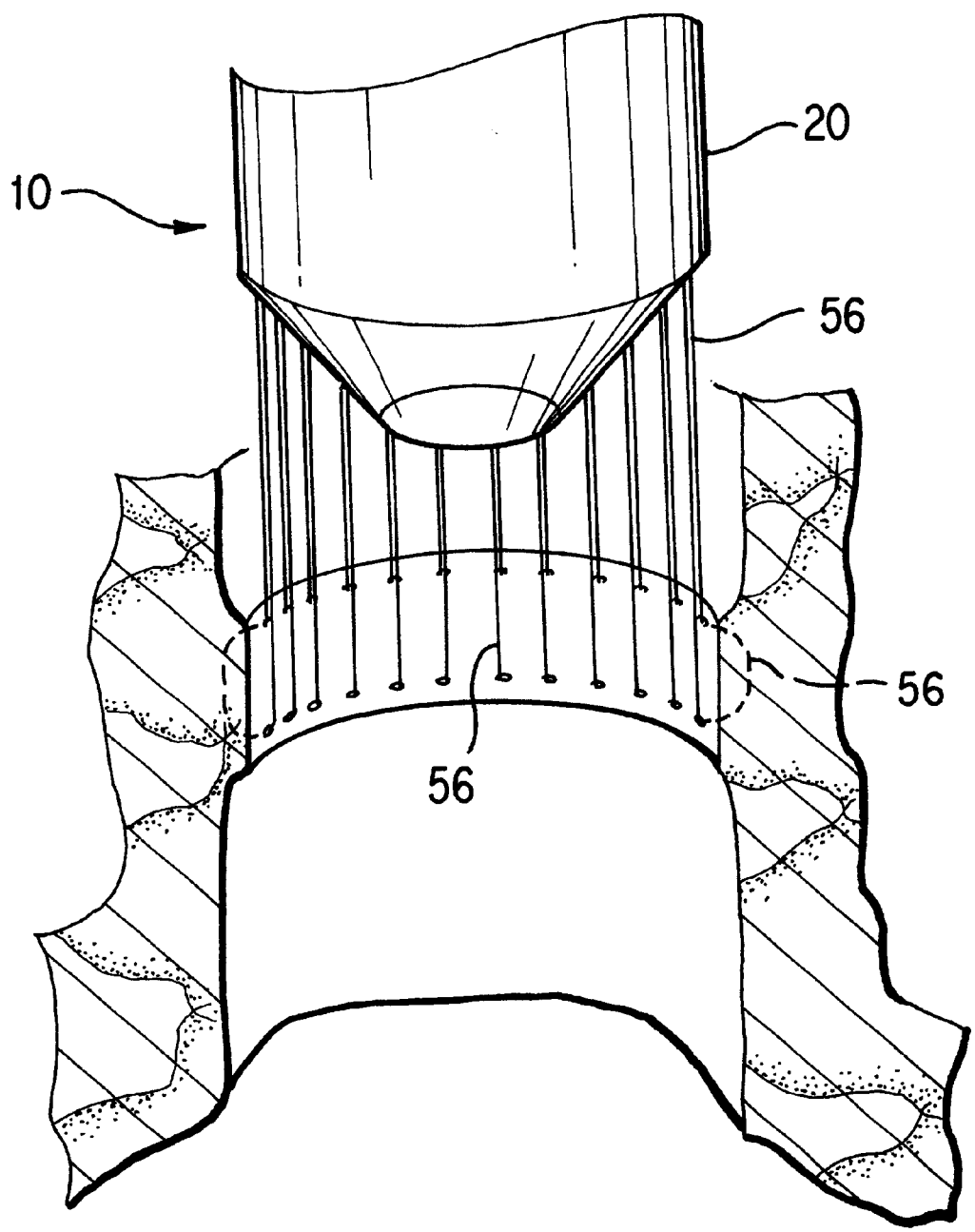
FIG. 4G is a view of FIG. 4F, in which the tube is being withdrawn from the surgical site leaving behind the sutures.

Still referring to FIG. 4G, the suture material 56 is pulled through the tissue as the needles 50 are lifted within the tube 20 as it is being withdrawn from the patient. Once the tissue has moved out of the suction opening, the device 10 can be carefully withdrawn from the surgical site, leaving behind a perfect cylinder of suture strands 56 in its path. Within the tube 20, the sutures 56 remain organized, in formation, as they are held by the engager 102 while the proximal end suture needles are releasably held in place.

When the tube 20 has been withdrawn sufficiently, the sutures 56 can be clamped and removed from the device 10. The interrupted sutures 56 can now be organized in a standard suture holder. As discussed above, at this point the sutures 56 are clamped in groups and removed from the tube 20. The sutures 56 are now ready to be incorporated into the chosen heart valve prosthesis or appropriate graft and lowered into position. The sutures 56 are tied and cut using minimally invasive instrumentation. The incisions needed to access the heart valve are now closed with suture and or surgical adhesives and the operation is completed in a standard fashion.

As one skilled in the art will appreciate, a similar procedure can be performed for mitral or other valve replacement, bioprostheses, homografts, allografts, repair of aneurysms in the aorta and other locations, vascular grafting, and endoluminal repair of arteries. Another advantageous use of the present invention is to repair sepal defects, a hole in the patient's heart between the chambers, which may require use of a tube 20 having a smaller size.

As also noted above, the present invention can be used in procedures that do not entail suturing annular tissue, but instead for suturing non-luminal tissues. In such a situation, the suction opening 30 is disposed laterally around only a portion of the circumference or perimeter of the tube 20 and the needles 50, correspondingly, would only be positioned to engage that portion of the tissue drawn into the suction opening 30.

In a related embodiment, it is also contemplated using the device 10 for suturing annular tissue in multiple steps. For example, if the suction opening 30 only extended around one third of the circumference of the tube 20, then the procedure could be performed in three sequential steps, in which each step involved one third of the annular tissue being sutured. Other fractions are also contemplated, such as the suction opening 30 extending laterally around one half of the circumference of the tube 20.

Although the present invention has been described with reference to specific details of certain embodiments thereof, it is not intended that such details should be regarded as limitations upon the scope of the invention except as and to the extent that they are included in the accompanying claims.

What is claimed is:

1. A suture device, comprising:

a. a tube having a distal end, a proximal end, and an exterior surface, the tube defining a bore longitudinally extending intermediate the distal and proximal ends and forming an interior surface of the tube, the tube further defining a suction opening laterally circumscribing at least a portion of the tube to allow fluid communication between the exterior surface and the bore;

b. a carriage for detachably holding at least one needle, the carriage having an outer periphery of a size to be complementarily and slidably received within the bore near the suction opening of the tube; and c. a lifter for moving the carriage within the bore of the tube toward the suction opening thereof.

2. The suture device of claim 1, further comprising a vacuum source in fluid communication with the bore of the tube, wherein the vacuum source is in fluid communication with the suction opening of the tube.

3. The suture device of claim 2, wherein the tube includes a vacuum port intermediate the suction opening and the proximal end thereof to which the vacuum source is operably connected.

4. The suture device of claim 1, further comprising an engager having an extender connected to a grasping portion which forms at least one slot, the slot being of a size to complementarily receive and detachably hold a portion of a needle therein, the grasping portion movable within the bore of the tube between an engaging position, in which the grasping portion of the engager is positioned near the suction opening, and a removing position, in which the grasping portion is positioned proximally relative to the engaging position.

5. The suture device of claim 1, wherein the periphery of the carriage defines at least one slit therein along a portion of the carriage, each slit being of a size to complementarily receive a bottom end of one respective needle.

6. The suture device of claim 5, wherein the needle received by the slit of the carriage is positioned between the carriage and the interior surface of the tube, and wherein, when the lifter moves the carriage proximally within the bore of the tube, the needle detachably held within the slit correspondingly slides along the interior surface of the tube toward the proximal end thereof.

7. The suture device of claim 1, wherein the lifter comprises a shaft having a lower end connected to a portion of the carriage and an upper end extending out of the proximal end of the tube so that, when a proximally-directed pulling force is applied to the shaft adjacent its upper end, the carriage moves proximally within the bore of the tube.

8. The suture device of claim 1, further comprising a plurality of longitudinally-extending arcuate struts, each arcuate strut having an upper end connected to a portion of the tube adjacent to the suction opening on the proximal side thereof, a lower end connected to a portion of the tube adjacent to the suction opening on the distal side thereof, and a body portion intermediate the upper and lower ends and disposed within the bore of the tube.

9. The suture device of claim 8, further comprising at least one laterally-oriented band, the band disposed within the bore of the tube and fixedly attached to a section of the body portion of each arcuate strut to circumscribe the arcuate struts.

10. The suture device of claim 1, further comprising means to inject a fluid into the bore of the tube so that the fluid is in communication with the suction opening of the tube.

11. A suture device, comprising:
    a. a tube having a distal end, a proximal end, and an exterior surface, the tube defining a bore longitudinally extending intermediate the distal and proximal ends and forming an interior surface of the tube, the tube further defining a suction opening laterally circumscribing at least a portion of the tube to allow fluid communication between the exterior surface and the bore;
    b. means for detachably holding at least one needle, the detachably holding means being movable within the bore intermediate the distal end and the suction opening of the tube; and
    c. means for moving detachably holding means within the bore of the tube toward the suction opening thereof.

12. The suture device of claim 11, wherein the detachably holding means comprises a carriage and wherein the moving means comprises a lifter.

13. The suture device of claim 11, further comprising a vacuum source in fluid communication with the bore of the tube, wherein the vacuum source is operably connected to the tube to be in fluid communication with the suction opening.

14. The suture device of claim 11, further comprising means to inject a fluid into the bore of the tube so that the fluid is in communication with the suction opening of the tube.

15. The suture device of claim 11, further comprising an engager having an extender connected to a grasping portion which forms at least one slot, the slot being of a size to complementarily receive and detachably hold a portion of a needle therein, the grasping portion movable within the bore of the tube between an engaging position, in which the grasping portion of the engager is positioned adjacent the suction opening, and a removing position, in which the grasping portion is positioned proximally relative to the engaging position.

16. A suture device, comprising:
    a. a tube having a distal end, a proximal end, and an exterior surface, the tube defining a bore longitudinally extending intermediate the distal and proximal ends and forming an interior surface of the tube, the tube further defining a suction opening laterally circumscribing at least a portion of the tube to allow fluid communication between the exterior surface and the bore;
    b. a vacuum source in fluid communication with the bore of the tube, wherein the vacuum source is operably connected to the tube to be in fluid communication with the suction opening;
    c. at least one needle having a bottom end and an opposed top end;
    d. a carriage for detachably holding the bottom end of the needle, the carriage having an outer periphery of a size to be complementarily and slidably received within the bore near the suction opening of the tube; and
    e. a lifter for moving the carriage within the bore of the tube toward the proximal end thereof.

17. The suture device of claim 16, further comprising an engager having an extender connected to a grasping portion which forms at least one slot, the slot being of a size to complementarily receive and detachably hold a portion of a needle therein, the grasping portion movable within the bore of the tube between an engaging position, in which the grasping portion of the engager is positioned adjacent the suction opening, and a removing position, in which the grasping portion is positioned proximally relative to the engaging position.

18. The suture device of claim 16, wherein the needle is a straight needle.

19. A method of suturing tissue, comprising the steps of:
    a. positioning a suction opening of a tube having a bore and an exterior surface adjacent to the tissue to be sutured;
    b. drawing a portion of the tissue to be sutured into the suction opening of the tube;
    c. moving at least one needle located within the bore of the tube to traverse the portion of the tissue that has been drawn into the suction opening, thereby placing suture into the tissue; and
    d. removing the tube from adjacent the tissue sutured in the moving step.

20. The method of claim 19, wherein the drawing step is performed using a vacuum source in fluid communication with the bore of the tube, wherein the vacuum source is operably connected to the tube to be in fluid communication with the suction opening.

21. The method of claim 19, after the moving step and before the removing step, further comprising the step of pushing the tissue sutured in the moving step out of the suction opening.

* * * * *